US00PP09063P

United States Patent [19]

Olesen et al.

[11] Patent Number: Plant 9,063

[45] Date of Patent: Feb. 28, 1995

[54] MINIATURE ROSE PLANT NAMED POULCLAUS

[75] Inventors: Mogens Olesen; Pernille Olesen, both of Fredensborg, Denmark

[73] Assignee: Weeks Wholesale Rose Grower, Inc., Upland, Calif.

[21] Appl. No.: 177,542

[22] Filed: Jan. 5, 1994

[51] Int. Cl.[6] ..... A01H 5/00

[52] U.S. Cl. ..... Plt./10

[58] Field of Search ..... Plt. 10, 28, 29

*Primary Examiner*—Howard J. Locker

*Attorney, Agent, or Firm*—Christie, Parker & Hale

[57] ABSTRACT

A new variety of miniature rose suitable for garden decoration, having flowers of deep red coloration.

1 Drawing Sheet

BACKGROUND OF THE INVENTION

This invention relates to a new and distinct variety of miniature rose. The varietal denomination of the new variety is 'Poulclaus'. The plant is dwarf bushy upright seedling cultivated for outdoor garden decoration. It has as its seed parent an unnamed seedling and as its pollen parent an unnamed seedling.

SUMMARY OF THE INVENTION

Among the features which distinguish the new variety 'Poulclaus' from other presently available and known commercial rose cultivars are the following combination of characteristics: its velvety red buds and flowers, its deep green highly disease-resistant foliage, its sepal interiors that blush red with age, and its fragrant stipitate glands carried on the outside of the bud. 'Poulclaus' may be asexually propagated by cuttings, budding, grafting, layering and tissue culture.

Asexual reproduction of the new variety as performed by budding in Kern County and Upland, Calif., shows that the foregoing and other distinguishing characteristics come true to form and are established and transmitted through succeeding propagations.

Comparison with Parent Varieties

The new rose may be distinguished from its seed parent, an unnamed seedling, by the following combination of characteristics: whereas 'Poulclaus' is classified as a Miniature with proportionately smaller leaves and flowers, the seed parent is classified as a Floribunda with significantly larger flowers and foliage. The new seedling has 14 to 18 petals whereas the seed parent has significantly more petals.

The new variety may be distinguished from its pollen parent, an unnamed seedling, by the following combination of characteristics: whereas the new cultivar bears flowers of a velvety red coloration with 14 to 18 petals, the pollen parent bears flowers of a coral coloration with significantly less petals. The pollen parent bears small foliage of a light green coloration, whereas 'Poulclaus' bears significantly larger foliage of a darker green color.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are in accordance with the Colour Chart of the Royal Horticultural Society of London, England, except where common terms of color definition are employed.

DESCRIPTION OF THE NEW VARIETY

The following descriptive matter pertains to roses of the new cultivar grown outdoors in Upland, Calif. in the month of August. Phenotypic expression may vary with environmental, cultural and climatic conditions, as well as differences in conditions of light and soil.

FLOWER

The new variety bears its flowers sometimes singly, usually five or more per stem. Flowers are borne in irregular rounded to pyramidal clusters on strong, medium to long stems for the class. Outdoors the plant blooms very abundantly and nearly continuously during the growing season. The flowers have a slight spicy fragrance.

BUD

The peduncle is of moderately long length for the class, of average to heavy caliper, and usually erect. It is moderately rough, with many stipitate glands and some hairs. Peduncle color is between 144A and 137A sometimes blushed on the sun side with near 183A. The peduncle is considered moderatly long for the class, nominally measuring about 4 to 5 cm. The overall bud size is considered large to medium long in length, measuring nominally about 2 to 2.5 cm in length and diameter at its widest point.

Before the calyx breaks, the bud is of medium to large size for the class, medium to long length, and pointed to ovoid in shape. The surface of the bud bears some foliaceous appendages and numerous stipitate glands, usually with slender-cut foliaceous parts extending beyond the tip of the bud equal to about three-quarters or more of its length. The stipitate glands carry an oil which exudes a moss rose fragrance, evidently due to some moss rose bud lines in the ancestry. Other varieties with moss rose characteristics include Peach Fuzz, Homey Moss and Honest Abe. Bud color is between 137A and 144A.

The inner surface of the sepals is covered with fine woolly tomentum; sepal margins are lined with many stipitate glands and hairs. Color of the inner surface of the sepal is between 191B and 193A. As the sepals begin to drop away from the petals, a blush color develops on the inner surface of between 48D and 52D toward the center and base. As the flower matures, the inner surface of the sepal blushes over the entire surface with a suffusion of between 48A and 53D.

As petals open, the bud is moderately large for the class, medium to long length, and very pointed to urn-shaped in form. The color of the outside surfaces of the newly opened petals is between 53A and 59A. The color of the inside surfaces of the newly opened petals is between 46A and 53A with a small basal attachment zone of near 155A in color. The bud opens up well and is generally not prevented from opening by wet, cold, hot or dry weather.

BLOOM

When fully open, the bloom is somewhat large for the class, ranging from 5 to 6.5 cm. in diameter. Petalage is semi-double with 14 to 18 petals and 1 to 3 petaloids arranged irregularly. When partially open, the bloom form is very high centered and the petals are moderately loosely spiraled to cupped with petal edges somewhat rolled outward. When fully open, the bloom form is somewhat more flat to cupped and the petals are somewhat less cupped to undulated with petal edges only slightly roller outward.

PETALS

The petals are moderately heavy in substance and of medium thickness, with inside surfaces very velvety and outside surfaces slightly shiny to satiny. The outer petals are very nearly round in shape with apices very rounded. The inside petals are broadly obovate in shape with apices somewhat rounded and sometimes slightly notched.

NEWLY OPENED FLOWER

The outside and inside surface of the outer, intermediate and inner petals is between 53A and 46A with a very small basal attachment zone of near 155A.

The general tonality of the newly opened flower is between 53A and 46A. The lighter white marking which may be perceived on some of the petals is considered an aberration, and not typical.

THREE-DAY-OLD FLOWER

The outside and inside surface of the outer and inner petals is between near 53A and near 46A.

The general tonality of the three day old flower is between 53A and 46A.

On the spent bloom, the petals usually drop off cleanly and are not particularly affected by cold, hot, wet or dry weather.

In August, blooms on the bush growing outdoors generally last from three to four days. Cut roses grown outdoors and kept at normal indoor living temperatures generally last from three to four or more days.

MALE REPRODUCTIVE ORGANS

Stamens are very abundant and are arranged regularly about the pistil; a few are mixed with petaloids. The filaments are irregular in length, most with anthers. The anthers are moderately large for the class and all open at approximately the same time. Anther color is between 25A and 168B when immature and near 166B at maturity. Pollen is very abundant and near 19A in color.

FEMALE REPRODUCTIVE ORGANS

Pistils are few in number (approximately 20). The styles are somewhat uneven, short to average in length, average in caliper, and somewhat loosely bunched. Stigma color is near 23D. Style color is near 53C. Ovaries are usually all enclosed in the calyx.

Hips when grown in Upland, Calif. are of moderately short in length, moderately ovoid to globular in form, and near 34C in color. The hip surface is very smooth with moderately thick fleshy walls. Seeds are few to average in number (approximately 8 to 17), and usually very small in size.

FOLIAGE

The compound leaves are usually comprised of three to five leaflets and are borne abundantly. The leaves are moderately large for the class, very heavy to crisp in texture, and somewhat glossy to semi-glossy in finish. The leaflets are shaped very oval with moderately acute apices and round bases. Their margins are usually simply serrate. Foliage size is considered moderately large for the class with full leaf measuring, nominally, about 8 to 9 cm long and about 4.5 to 4.5 cm across at its widest point. The individual leaflets measure nominally about 2.5 to 3 cm long and about 2 to 2.5 cm wide at their widest point. Stem length is considered medium to long, ranging nominally from about 8 to 15 cm.

The upper surface of the mature leaf is between 137A and 139A. The under surface of the mature leaf is between 191A and 191B. The upper surface of the young leaf is between 146A and 137A, sometimes very lightly suffused with near 183C at the very edge of the leaf. The under surface of the young leaf is between 146B and 139C, sometimes lightly suffused with near 183C.

The rachis is average in caliper and somewhat rough with many stipitate glands on the edges of the upper side. The under side of the rachis is somewhat rough with many stipitate glands and some very small prickles.

The stipules are medium to long in length with medium width and moderately long straight points that usually turn out at an angle of less than 45 degrees.

The plant displays a well above average degree of resistance to powdery mildew, blackspot and rust as compared to other commercial varieties grown under comparable conditions in Upland, Calif.

GROWTH

The plant has a bushy, compact, upright, medium height habit with very full branching. It displays very vigorous growth and the canes are of moderately heavy caliper for the class. Characteristic plant height and spread is considered dwarf, bushy, and upright, but medium tall for the class. Mature height measurement and spread in California is about 65 to 75 cm.

The color of the major stems are near 146D. They bear few large prickles which are somewhat long for the class. The large prickles are almost straight angled slightly downward with a moderately short somewhat broad to rounded base; prickle color is near 161B. The major stems bear no small prickles.

The color of the branches are between 144B and 137C. They bear several large prickles and few small prickles which are somewhat long for the class. The prickles are almost straight angles slightly downward with a moderately short, somewhat broad to rounded base; prickle color is near 160B.

The color of the new shoots are between 144A and 146C sometimes lightly suffused with near 183B. Then bear several large prickles and few small prickles which are somewhat long for the class. The prickles are almost straight angled slightly downward with a moderately short somewhat broad to rounded base; prickle color is near 173B.

We claim:

1. A new and distinct variety of miniature rose plant substantially as described and illustrated herein.

* * * * *

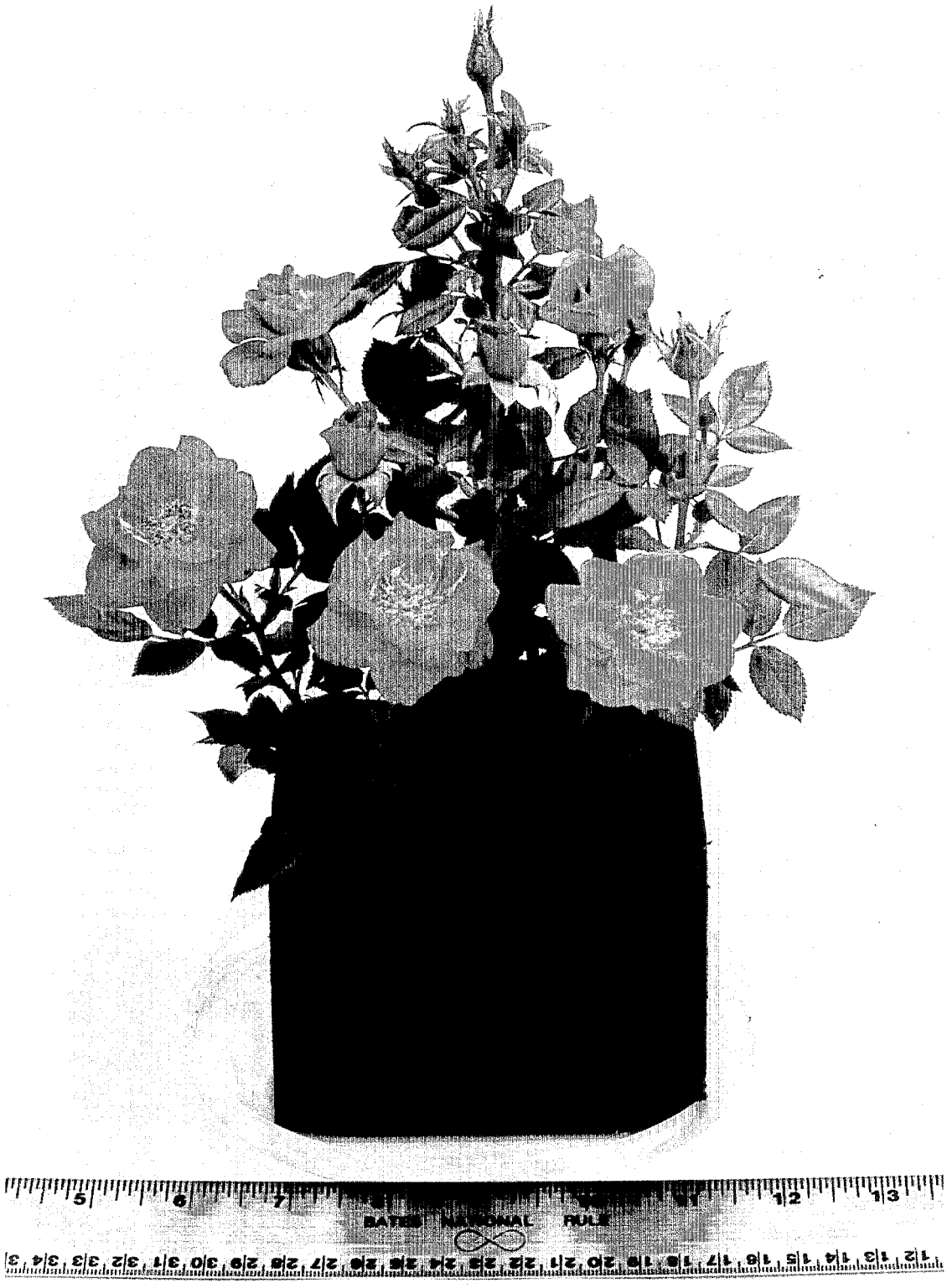
BATES NATIONAL RULE

UNITED STATES PATENT AND TRADEMARK OFFICE

CERTIFICATE OF CORRECTION

PATENT NO. : Plant 9,063

DATED : February 28, 1995

INVENTOR(S) : Mogens Olesen; Pernille Olesen

It is certified that error appears in the above-indentified patent and that said Letters Patent is hereby corrected as shown below:

Column 1, line 5, before "dwarf" insert -- a --.

Column 2, line 28, change "moderatly" to -- moderately --.

Column 3, line 23, change "roller" to -- rolled --.

Column 4, line 60, change "Then" to -- They --.

Signed and Sealed this

Fifth Day of September, 1995

*Attest:*

*Attesting Officer*

Bruce Lehman

BRUCE LEHMAN

*Commissioner of Patents and Trademarks*